(12) United States Patent
Sakaguchi et al.

(10) Patent No.: US 9,095,258 B2
(45) Date of Patent: Aug. 4, 2015

(54) X-RAY IMAGING APPARATUS AND PROGRAM

(71) Applicants: KABUSHIKI KAISHA TOSHIBA, Tokyo (JP); Toshiba Medical Systems Corporation, Otawara-shi (JP)

(72) Inventors: Takuya Sakaguchi, Utsunomiya (JP); Manabu Tanaka, Otawara (JP); Takayuki Ishikawa, Nasushiobara (JP); Hisato Takemoto, Nasushiobara (JP); Koichiro Watanabe, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 219 days.

(21) Appl. No.: 13/738,254

(22) Filed: Jan. 10, 2013

(65) Prior Publication Data

US 2013/0182822 A1 Jul. 18, 2013

(30) Foreign Application Priority Data

Jan. 12, 2012 (JP) ................................. 2012-004390

(51) Int. Cl.
*A61B 6/02* (2006.01)
*A61B 6/00* (2006.01)

(52) U.S. Cl.
CPC ................ *A61B 6/022* (2013.01); *A61B 6/487* (2013.01); *A61B 6/503* (2013.01); *A61B 6/5288* (2013.01); *A61B 6/542* (2013.01); *A61B 6/4464* (2013.01)

(58) Field of Classification Search
USPC ......... 378/147, 148, 149, 150, 151, 152, 153, 378/162, 165, 204, 205
See application file for complete search history.

(56) References Cited

U.S. PATENT DOCUMENTS

| 2006/0104420 | A1* | 5/2006 | Mollus .......................... 378/147 |
| 2006/0280288 | A1 | 12/2006 | Speiser et al. |
| 2010/0054413 | A1* | 3/2010 | Sobering et al. ................ 378/65 |

FOREIGN PATENT DOCUMENTS

| CN | 1636512 A | 7/2005 |
| CN | 1637435 A | 7/2005 |
| JP | 2002-6046 A | 1/2002 |

(Continued)

OTHER PUBLICATIONS

Combined Chinese Office Action and Search Report issued Jul. 25, 2014, in Chinese Patent Application No. 201310011767.X with English translation.

(Continued)

*Primary Examiner* — Nicole Ippolito
(74) *Attorney, Agent, or Firm* — Oblon, McClelland, Maier & Neustadt, L.L.P.

(57) ABSTRACT

According to one embodiment, an X-ray imaging apparatus includes an X-ray generation unit, an X-ray collimator, a dose detection unit, and a dose reduction rate calculation unit. The X-ray generation unit irradiates the object with X-rays. The X-ray collimator limits an X-ray irradiation range of the X-ray generation unit. The dose detection unit detects the X-rays that have passed through the X-ray collimator. The dose reduction rate calculation unit calculates a reduction rate of an exposure dose of the object based on a value detected by the dose detection unit in X-ray imaging before the X-ray irradiation range is limited by the X-ray collimator and a value detected by the dose detection unit in X-ray imaging after the X-ray irradiation range is limited by the X-ray collimator.

7 Claims, 6 Drawing Sheets

(56) References Cited

FOREIGN PATENT DOCUMENTS

| | | |
|---|---|---|
| JP | 2003-265499 | 9/2003 |
| JP | 2006-517439 | 7/2006 |
| JP | 2010-68978 | 4/2010 |
| JP | 2012-75782 | 4/2012 |

OTHER PUBLICATIONS

Office Action mailed Jun. 9, 2015 in Japanese Application No. 2012-004390 filed Jan. 12, 2012.

* cited by examiner

X-RAY IMAGING APPARATUS AND PROGRAM

CROSS-REFERENCE TO RELATED APPLICATIONS

This application is based upon and claims the benefit of priority from Japanese Patent Application No. 2012-004390, filed Jan. 12, 2012, the entire contents of which are incorporated herein by reference.

FIELD

Embodiments described herein relate generally to an X-ray imaging apparatus and a program.

BACKGROUND

To treat an ischemic heart disease, an intravascular treatment that is a minimally invasive treatment is often employed in recent years. The intravascular treatment is conducted fluoroscopically using an X-ray imaging apparatus. The intravascular treatment may need two to three hrs to give, and the dose of the patient and medical staff poses a problem. Hence, to reduce the dose, the object is protected using a protective plate, or the imaging rate is decreased. However, the X-ray dose reduction effect of these measures is not sufficient.

On the other hand, a technique called ROI fluoroscopy is known (for example, Jpn. Pat. Appln. KOKAI Publication No. 2003-265449). ROI fluoroscopy is a technique of performing X-ray imaging only for a region of interest designated by the operator. Adopting the ROI fluoroscopy allows to actually properly reduce the exposure dose of the object as compared to a case in which normal X-ray imaging is executed.

However, the operator of the X-ray imaging apparatus cannot know specifically how much the exposure dose is decreased as compared to normal X-ray imaging.

It is an object to provide an X-ray imaging apparatus that allows the operator to recognize the degree of exposure dose reduction implemented by executing ROI fluoroscopy as compared to a case in which normal X-ray imaging apparatus is (to be) executed, and a program.

DETAILED DESCRIPTION

In general, according to one embodiment, an X-ray imaging apparatus for performing X-ray imaging of an object and acquiring an X-ray fluoroscopic image includes an X-ray generation unit, an X-ray collimator, a dose detection unit, and a dose reduction rate calculation unit.

The X-ray generation unit is configured to irradiate the object with X-rays.

The X-ray collimator is configured to limit an X-ray irradiation range of the X-ray generation unit.

The dose detection unit is configured to detect the X-rays that have passed through the X-ray collimator.

The dose reduction rate calculation unit is configured to calculate a reduction rate of an exposure dose of the object based on a value detected by the dose detection unit in X-ray imaging before the X-ray irradiation range is limited by the X-ray collimator and a value detected by the dose detection unit in X-ray imaging after the X-ray irradiation range is limited by the X-ray collimator.

An X-ray imaging apparatus according to an embodiment of the present invention will now be described with reference to the accompanying drawings.

Figure 1:
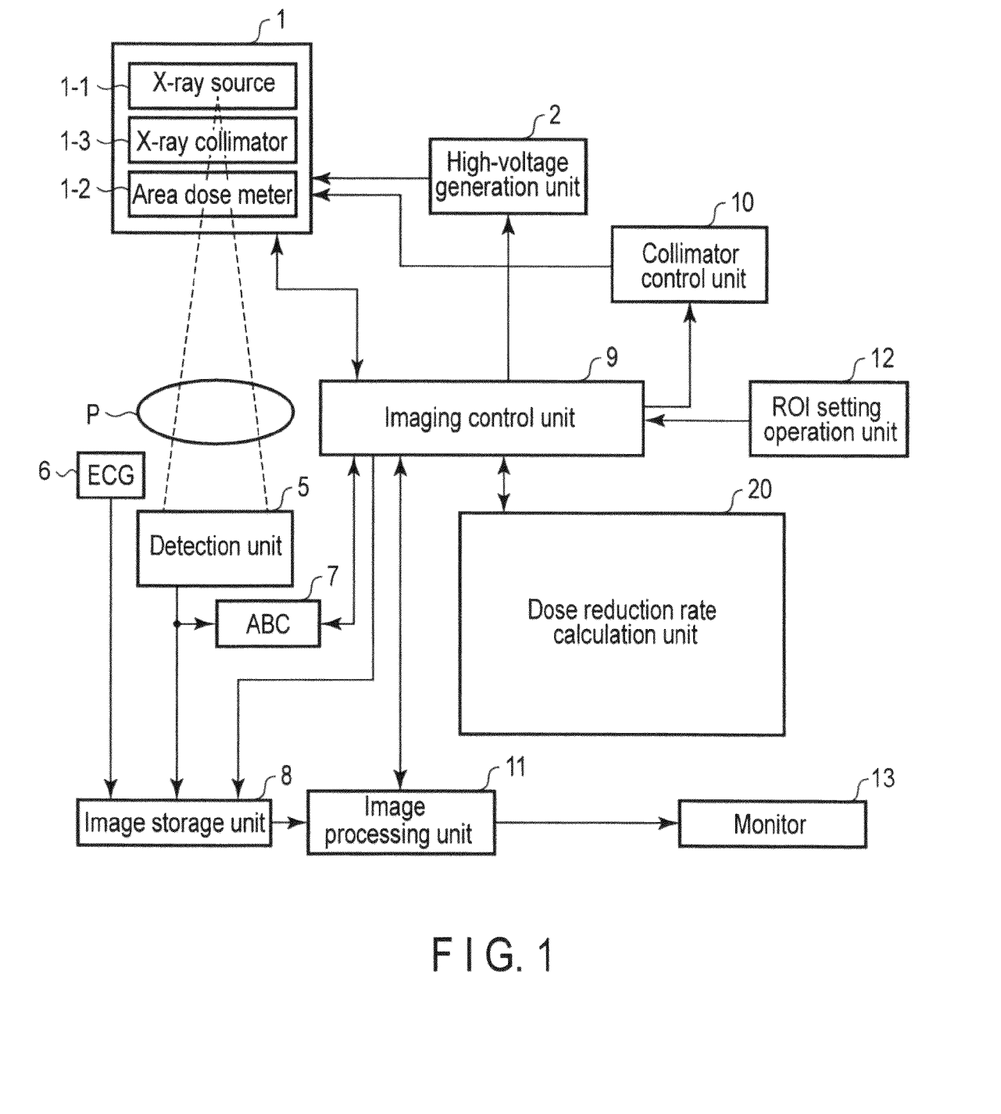
FIG. 1 is a block diagram showing an example of the system arrangement of an X-ray imaging apparatus according to an embodiment of the present invention.
Figure 2:
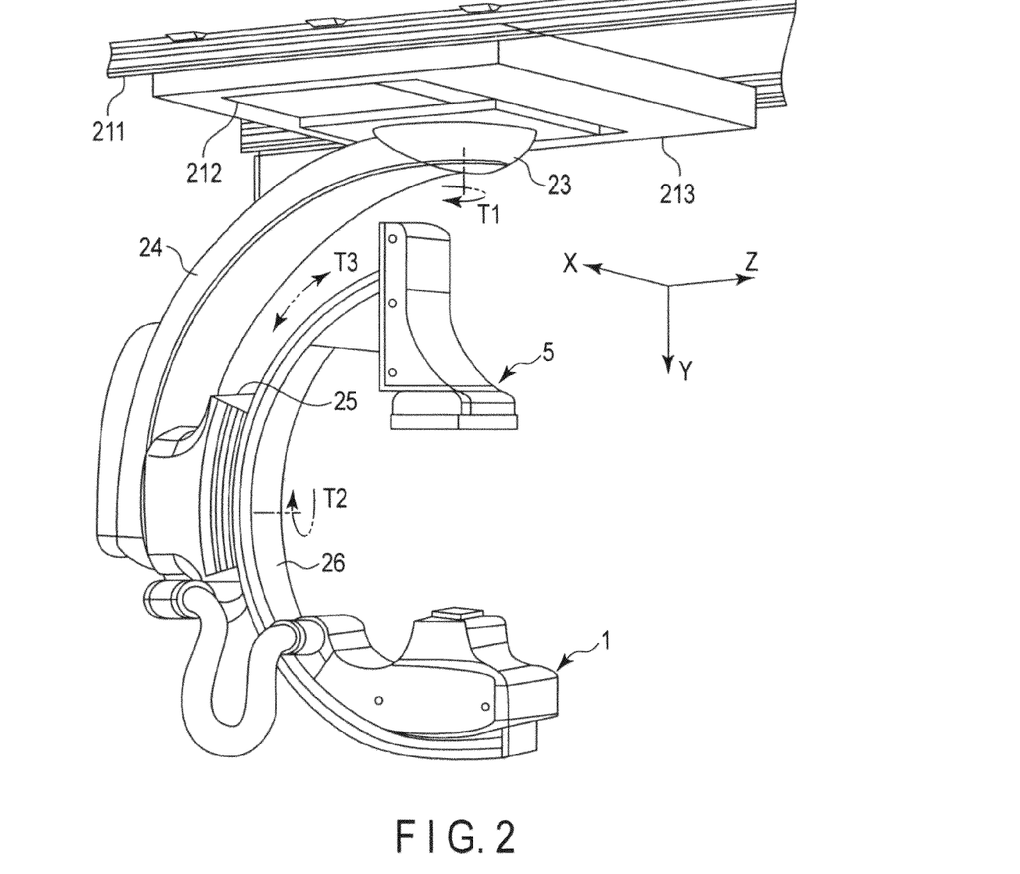
FIG. 2 is an outside perspective view showing an example of the structure of an imaging mechanism including an X-ray irradiation unit shown in FIG. 1.

FIG. 1 is a block diagram showing an example of the system arrangement of the X-ray imaging apparatus according to an embodiment of the present invention. FIG. 2 is an outside perspective view showing an example of the structure of an imaging mechanism including an X-ray irradiation unit 1 shown in FIG. 1.

As shown in FIG. 1, the X-ray imaging apparatus comprises the X-ray irradiation unit 1 including an X-ray source 1-1, an area dose meter 1-2, and an X-ray collimator 1-3, a high-voltage generation unit 2, an X-ray detection unit 5, an ECG (electrocardiograph) 6, an ABC (Automatic Brightness Control) 7, an image storage unit 8, an imaging control unit 9, a collimator control unit 10, an image processing unit 11, an ROI setting operation unit 12, a monitor 13, and a dose reduction rate calculation unit 20 as the system arrangement.

As shown in FIG. 2, the X-ray imaging apparatus comprises a Z-axis rail direction 211, an X-axis direction rail 212, a carriage 213, a vertical axis rotating mechanism 23, a suspended arm 24, a C-arm rotating mechanism 25, a C-arm 26, the X-ray irradiation unit 1, and the X-ray detection unit 5 as the components concerning the imaging mechanism.

Note that the X-ray imaging apparatus shown in FIG. 2 is a so-called under-tube type X-ray imaging apparatus. However, this embodiment is also applicable to an X-ray imaging apparatus of any other type (for example, over-tube type).

The Z-axis direction rail 211, the X-axis direction rail 212, and the carriage 213 constitute a slide mechanism. The slide mechanism formed from the Z-axis direction rail 211, the X-axis direction rail 212, and the carriage 213 slides the vertical axis rotating mechanism 23, the suspended arm 24, the C-arm rotating mechanism 25, the C-arm 26, the X-ray irradiation unit 1, and the X-ray detection unit 5 integrally in the horizontal direction under the control of a driving control unit (not shown).

The Z-axis direction rail 211 is extended in a Z-axis direction shown in FIG. 2 and supported by a ceiling. The X-axis direction rail 212 is extended in an X-axis direction shown in FIG. 2 and supported by the Z-axis direction rail 211 via rollers (not shown) at both ends of the X-axis direction rail 212. The X-axis direction rail 212 moves in the Z-axis direction on the Z-axis direction rail 211 under the control of a driving control unit (not shown).

The carriage 213 is supported by the X-axis direction rail 212 via a roller (no shown). The carriage 213 moves in the X-axis direction on the X-axis direction rail 212 under the control of the driving control unit (not shown).

The X-axis direction rail 212 that supports the carriage 213 is movable in the Z-axis direction on the Z-axis direction rail 211. The carriage 213 is movable in the X-axis direction on the X-axis direction rail 212. Therefore, the carriage 213 is movable in the horizontal direction (the X-axis direction and the Z-axis direction) within the examination room in which the X-ray imaging apparatus is installed.

The vertical axis rotating mechanism 23 is rotatably supported by the carriage 213. The vertical axis rotating mechanism 23 rotates the suspended arm 24, the C-arm rotating mechanism 25, the C-arm 26, the X-ray irradiation unit 1, and the X-ray detection unit 5 integrally in a vertical axis rotating direction T1 under the control of the driving control unit (not shown).

The suspended arm 24 is supported by the vertical axis rotating mechanism 23.

The C-arm rotating mechanism 25 is rotatably supported by the suspended arm 24. The C-arm rotating mechanism 25 rotates the C-arm 26, the X-ray irradiation unit 1, and the X-ray detection unit 5 integrally in a rotating direction T2 with respect to the suspended arm 24 under the control of the driving control unit (not shown).

The C-arm 26 is supported by the C-arm rotating mechanism 25. On the C-arm 26, the X-ray irradiation unit 1 and the X-ray detection unit 5 are arranged to face each other across an object P. A rail (not shown) is provided on the back or a side of the C-arm 26. The rail is sandwiched between the C-arm rotating mechanism 25 and the C-arm 26. The C-arm 26 moves, via the rail (not shown), the X-ray irradiation unit 1 and the X-ray detection unit 5 to draw an arcuate orbit integrally in an arc direction T3 of the C-arm 26. This movement is also done under the control of the driving control unit (not shown).

The X-ray irradiation unit 1 is provided at one end of the C-arm 26. The X-ray irradiation unit 1 is provided to be movable back and forth under the control of the driving control unit (not shown).

The X-ray source 1-1 is connected to the high-voltage generation unit 2. The X-ray source 1-1 receives supply of high-voltage power from the high-voltage generation unit 2 and irradiates a predetermined part of the object P with X-rays in accordance with the condition of the high-voltage power.

The high-voltage generation unit 2 supplies a current (filament current) to the filament of the X-ray source 1-1. The X-ray source 1-1 thus generates X-rays and irradiates the object P with them. The tube voltage and the filament current of the high-voltage generation unit 2 can independently be changed.

The X-ray detection unit 5 is provided at the other end of the C-arm 26 (on an emission side of the X-ray irradiation unit 1). The X-ray detection unit 5 is provided to be movable back and forth under the control of the driving control unit (not shown). The X-ray detection unit 5 is, for example, an FPD (Flat Panel Detector) formed by two-dimensionally arraying a plurality of detection elements (pixels) which directly or indirectly convert incident X-rays into charges. The X-ray detection unit 5 detects the X-rays by the detection elements and converts them into an electrical signal. At the time of imaging, the object P is placed on the top of a bed and, in that state, arranged between the X-ray source 1-1 and the X-ray detection unit 5.

The imaging control unit 9 systematically controls the entire X-ray imaging apparatus according to this embodiment. The imaging control unit 9 supplies first and second control signals to the high-voltage generation unit 2 at the time of X-ray imaging. The first control signal changes the tube voltage applied from the high-voltage generation unit 2 to the X-ray source 1-1. The second control signal changes the filament current supplied from the high-voltage generation unit 2 to the X-ray source 1-1. The change in the tube voltage and that in the filament current cause a change in the exposure of the object P to the X-rays.

The X-ray collimator 1-3 is arranged in the X-ray radiation window of the X-ray source 1-1. The X-ray collimator 1-3 restricts (limits) the irradiation range (X-ray irradiation range) of the X-rays emitted from the X-ray source 1-1 to the object P. Although not illustrated, the X-ray collimator 1-3 comprises, for example, a plurality of individually movable shield plates. The X-ray irradiation range is limited to a rectangular range or a rectangular or circular range tilted with respect to the X-axis by the number of shield plates and variations of moving methods. For example, the number of shield plates is four, and the X-ray irradiation range is rectangular. The shield plates are typically formed from lead plates having an X-ray shielding effect. However, wedges, for example, molybdenum-containing plates that have translucency against X-rays to change their quality may originally be used.

The collimator control unit 10 controls the movement of the shield plates provided in the X-ray collimator 1-3. This allows to arbitrarily change the center position and size of the aperture surrounded by the shield plates, for example, the diagonal length and diameter of the aperture.

The area dose meter 1-2 is a dosimeter that detects the dose (exposure dose) of X-rays emitted from the X-ray source 1-1 and passed through the X-ray collimator 1-3 at an arbitrary detection period. The area dose meter 1-2 includes a conversion element that converts the dose of incident X-rays into charges. The area dose meter 1-2 generates a signal representing an area dose (represented by, for example, $[Gy \cdot cm^2]$; to be referred to as an exposure dose hereinafter) almost proportional to the irradiation intensity, irradiation area, and irradiation time of X-rays in the area dose meter 1-2 and an area dose ratio (represented by, for example, $[Gy \cdot cm^2/s]$; to be referred to as an exposure dose rate hereinafter) and outputs the signal.

Note that imaging performed by irradiating a limited part of the light-receiving surface of the X-ray detection unit 5 with X-rays is referred to as partial imaging or ROI fluoroscopy. ROI stands for Region Of Interest, that is, a region of interest that can be defined as a partial region within an imaging range to be closely observed with intensive interest. The irradiation range at this time will be referred to as a second irradiation range. The irradiation range is typically defined as the size of a region where an X-ray beam intersects an imaging reference surface that passes through the iso-center and perpendicularly crosses the X-ray central axis. Imaging in the second irradiation range is the above-described ROI fluoroscopy, and the aperture of the X-ray collimator 1-3 corresponding to the second irradiation range will be referred to as a partial aperture.

An irradiation range (in this example, an irradiation range without being limited by the X-ray collimator 1-3) wider than the second irradiation range will be referred to as a first irradiation range. That is, the first irradiation range corresponds to the entire light-receiving surface of the X-ray detection unit 5. Imaging in the first irradiation range will be referred to as full field imaging, and the aperture corresponding to the first irradiation range will be referred to as a full aperture.

In this embodiment, the first irradiation range will be explained as a region corresponding to the whole light-receiving region of the X-ray detection unit 5. However, the first irradiation range may be a region narrower than the region corresponding to the whole light-receiving region of the X-ray detection unit 5 as long as it is a region wider than at least the second irradiation range.

Note that the center position and size of the second irradiation range within the first irradiation range can arbitrarily be changed under the control of the collimator control unit 10.

The ROI setting operation unit 12 is an operation unit configured to set a region of interest (to be referred to as a ROI hereinafter) in a full display image on the monitor 13. The ROI range information set by the operator's operation of the ROI setting operation unit 12 is supplied to the imaging control unit 9 together with a control signal used to change the aperture state of the X-ray collimator 1-3.

In ROI fluoroscopy according to ROI set by the ROI setting operation unit 12, the imaging control unit 9 supplies information about the position and size of the ROI to the ABC 7.

The ABC 7 extracts data corresponding to the ROI from the output of the X-ray detection unit 5, compares an average value or the like representing the exposure amount with a predetermined threshold, and supplies the comparison result to the imaging control unit 9. In ROI fluoroscopy, scatter out of the X-rays entering the object P decreases. For this reason, image data acquired by X-ray imaging becomes slightly darker in ROI fluoroscopy than in full field imaging. Hence, upon receiving the compression result supplied from the ABC 7, the imaging control unit 9 increases the radiation dose in the X-ray imaging by increasing at least one of the tube current, the tube voltage, and the X-ray pulse width so as to control the image data brightness to almost the same level as in full field imaging.

The image storage unit 8 stores image data acquired by the X-ray detection unit 5 repetitively at a predetermined period during a period in which X-ray irradiation continues. These image data are displayed on the monitor 13 via the image processing unit 11 in real time.

The image storage unit 8 stores image data captured by the X-ray detection unit 5. The ECG (electrocardiograph) 6 measures the electrocardiographic complex of the object P, analyzes the electrocardiographic complex, and outputs data representing the cardiac phase. The cardiac phase is, for example, an index obtained by normalizing each position of a period (one heartbeat period) from an R-wave to the next R-wave by percentage. Cardiac phase data corresponding to an imaging time is associated with each image data stored in the image storage unit 8. The image data stored in the image storage unit 8 is displayed on the monitor 13 via the image processing unit 11. The monitor 13 is installed in, for example, a Cath-Lab together with the imaging mechanism shown in FIG. 2.

The dose reduction rate calculation unit 20 calculates an "index representing the X-ray dose reduction effect" obtained by causing the to X-ray collimator 1-3 to limit the X-ray irradiation range of the X-ray source 1-1 (details will be described later).

Note that as the "exposure dose", an incident dose to the area dose meter 1-2, a dose (absorbed dose or dose equivalent) calculated by the area dose meter 1-2, an exposure of the object P, or the like is usable. For the descriptive convenience, the dose (the output value of the area dose meter 1-2) calculated by the area dose meter 1-2 will be explained as the "exposure dose". As a detailed method of measuring the exposure dose, a method by actual measurement using the detected value of the area dose meter 1-2 and a method of calculating the exposure dose using various conditions concerning X-ray irradiation can mainly be used (details will be described later).

In this embodiment, the X-ray imaging apparatus is assumed to be an apparatus including a ceil mounted C-arm as shown in FIG. 2. However, the present invention is not limited to this. That is, this embodiment is also applicable to, for example, an apparatus including a floor mounted C-arm.

Figure 3:
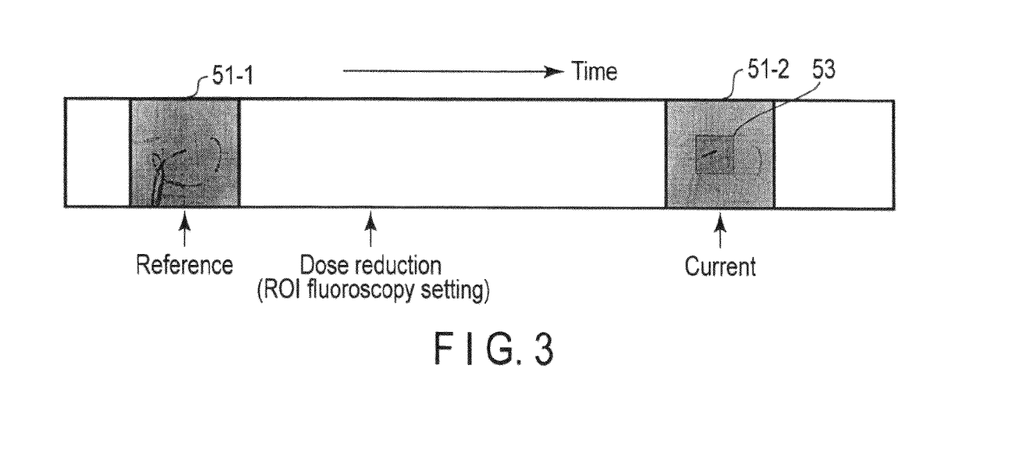
FIG. 3 is a view showing the schematic procedure of processing of calculating an "index representing the X-ray dose reduction effect" by the X-ray imaging apparatus according to an embodiment of the present invention.

FIG. 3 is a view showing the schematic procedure of processing of calculating the "index representing the X-ray dose reduction effect" by the X-ray imaging apparatus according to the embodiment of the present invention.

First, full field imaging is executed. More specifically, the aperture of the X-ray collimator 1-3 is set in a full aperture state. After the start of manipulation, the imaging control unit 9 controls the high-voltage generation unit 2 so as to cause the X-ray source 1-1 to start generating X-rays based on a trigger input by the operator at an appropriate timing and irradiate the object P with the X-rays.

At this time, the X-rays irradiate the object P within the first irradiation range. X-ray irradiation continues until the operator returns the apparatus to the neutral state. During the period when the X-ray irradiation is continuing, the X-ray detection unit 5 repetitively acquires image data at a predetermined period. The acquired image data is stored in the image storage unit 8 and simultaneously displayed on the monitor 13 via the image processing unit 11 in real time. The image data acquired by the above-described full field imaging is, for example, full image data 51-1 shown in FIG. 3. The area of the X-ray irradiation range in this full field imaging is set as a "reference area", and the exposure dose is set as a "baseline".

After that, when X-ray generation is stopped by the operator's operation, the imaging control unit 9 controls the high-voltage generation unit 2 to stop X-ray generation and stop X-ray irradiation. The full field imaging thus stops.

The operator performs X-ray dose reduction processing here. More specifically, the operator sets an ROI in the full display image displayed on the monitor 13 using the ROI setting operation unit 12. The imaging control unit 9 controls the collimator control unit 10 to change the aperture state of the X-ray collimator 1-3 based on the ROI range information and a control signal supplied from the ROI setting operation unit 12.

By this control, the collimator control unit 10 changes the aperture state of the X-ray collimator 1-3 from the full aperture state to a partial aperture state corresponding to the set ROI. In other words, the X-ray irradiation range is changed from the first irradiation range to the second irradiation range under the control of the collimator control unit 10.

When the above-described change in the aperture state is completed, the imaging control unit 9 controls the high-voltage generation unit 2 so as to start generating X-rays and start irradiating the object with the X-rays, thereby starting X-ray irradiation. In synchronism with the start of X-ray irradiation, the imaging control unit 9 causes the X-ray detection unit 5 to start acquiring image data (partial image data by ROI fluoroscopy). The acquired partial image data is stored in the image storage unit 8 and simultaneously displayed on the monitor 13 via the image processing unit 11 in real time as a moving image.

Figure 4:
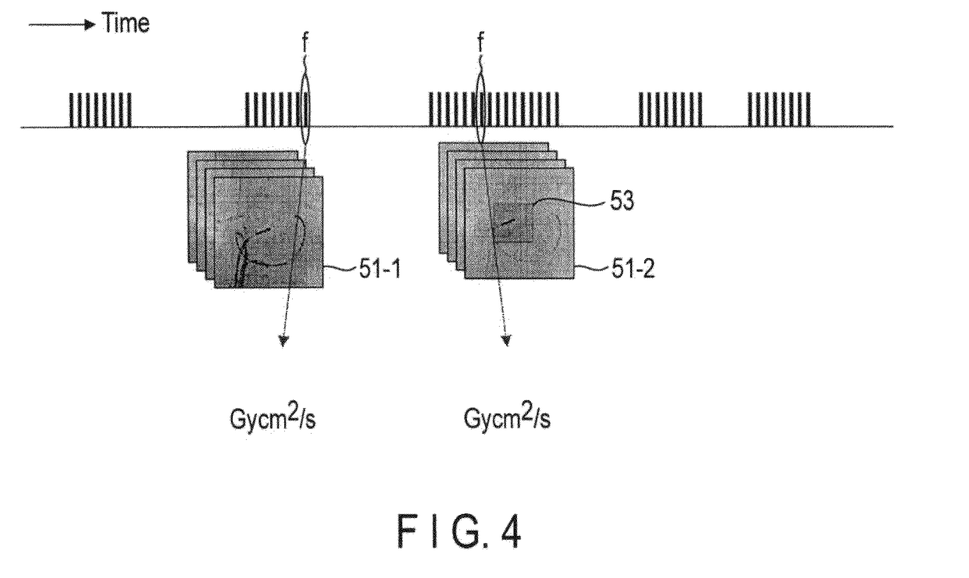
FIG. 4 is a view showing the concept of an exposure dose rate that is an exposure dose per frame (per sec)
Figure 5A:
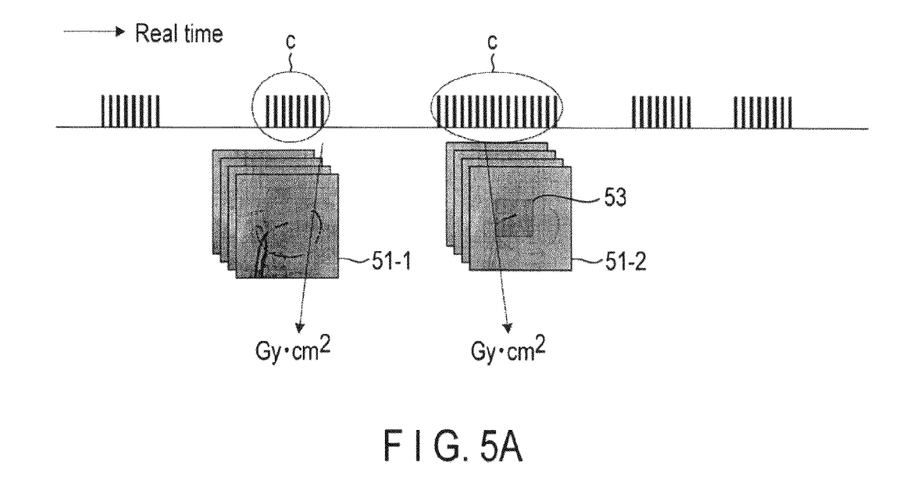
FIG. 5A is a view showing the concept of the exposure dose that is perceived as a cumulative amount during the X-ray irradiation operation period corresponding to one run from the starting point of the X-ray irradiation operation to the end point of the operation.
Figure 5B:
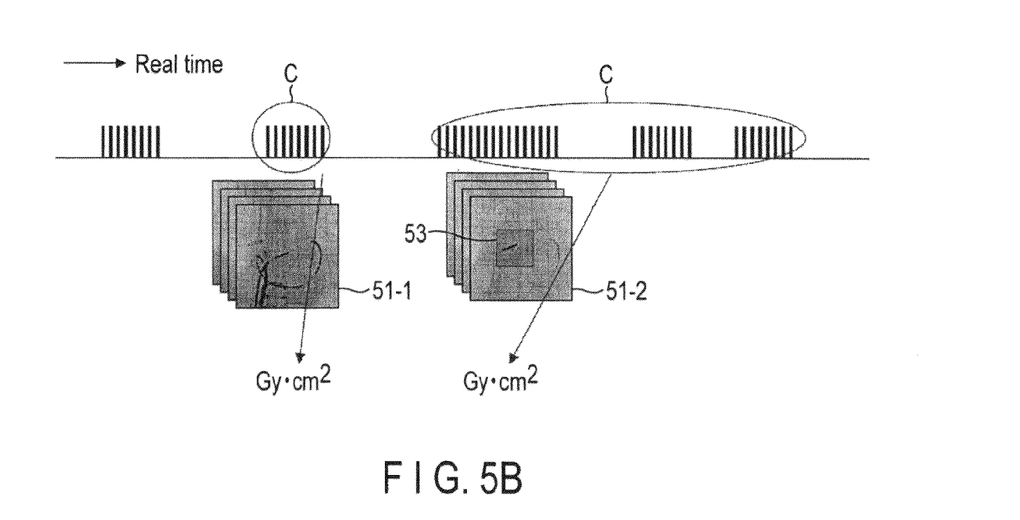
FIG. 5B is a view showing the concept of the exposure dose that is perceived as a cumulative amount during a series of manipulation periods including one or more runs.

Various perspectives of the "exposure dose" according to this embodiment will be described below with reference to FIGS. 4, 5A, and 5B. FIG. 4 is a view showing the concept of the exposure dose rate that is an exposure dose per frame (for each frame). FIG. 5A is a view showing the concept of the exposure dose that is perceived as a cumulative amount during the X-ray irradiation operation period corresponding to one run from the starting point of the X-ray irradiation operation to the end point of the operation. FIG. 5B is a view showing the concept of the exposure dose that is perceived as a cumulative amount during a series of manipulation periods including one or more runs.

The perspectives of the exposure dose according to this embodiment can roughly be classified into following two types.

As one perspective, the exposure dose is perceived as an amount per frame (per second) (exposure dose rate). That is, the exposure dose is perceived as an amount per frame (for example, per 1 second), as shown in FIG. 4. In this case, the unit of the exposure dose rate is, for example, "Gy/s" or "Gy·cm²/s".

As another perspective, the exposure dose is perceived as a cumulative amount during a predetermined period, as shown in FIGS. 5A and 5B.

In the example shown in FIG. 5A, the exposure dose is perceived as a cumulative amount during a series of X-ray irradiation operation periods (a period called one cut or one run; a period c in FIG. 5A) from the starting point of the X-ray irradiation operation to the end point of the operation. The X-ray irradiation operation indicates, for example, pressing an X-ray irradiation switch (not shown), and the end of the operation indicates, for example, taking the hand off the X-ray irradiation switch (not shown). One run is normally 3 to 30 sec.

In the example shown in FIG. 5B, the exposure dose is perceived as a cumulative amount during the series of manipulation periods C including one or more runs. In other words, in this example, the exposure dose is perceived in consideration of the whole operation. The exposure dose is perceived as a total cumulative amount in all runs of imaging during an arbitrary section (normally from the beginning to the current point) of the operation time (at least 15 min, and if long, 3 hrs or more).

In the above-described examples shown in FIGS. 5A and 5B, the unit of the exposure dose is, for example, "Gy" or "Gy·cm²".

The images acquired in each run are saved as one file of moving image in a block for each run. The doctor can rest or perform an operation of, for example, setting an ROI between the runs.

More specifically, as shown in FIG. 3, partial image data 53 displayed in real time is aligned to full image data 51-2 acquired in the immediately preceding full field imaging period and stored in the image storage unit 8 and combined (for example, superimposed) by the image processing unit 11.

That is, the image processing unit 11 trims the image (partial image data 53) corresponding to the ROI and superimposes it on the full image data 51-2 acquired in the immediately preceding full field imaging period and stored.

Note that the full image to be combined with the partial image can be either a reproduced moving image or the still image of a specific frame out of a plurality of still images included in the moving image, for example, the still image of the last frame in the immediately preceding full field imaging period.

Examples of calculation by the dose reduction rate calculation unit 20 of the X-ray imaging apparatus according to the embodiment will be described below. The dose reduction rate calculation unit 20 calculates the following "indices representing the X-ray dose reduction effect" based on information supplied from the imaging control unit 9.

Note that all the following "indices representing the X-ray dose reduction effect" or a predetermined index preset in accordance with the user's purpose is combined with the full image data by the image processing unit 11 and displayed on the monitor 13.

<Index 1>
S2/S1 that is the ratio of an "area S2 of the X-ray irradiation range (second irradiation range) after limited by the X-ray collimator 1-3" to an "area S1 of the X-ray irradiation range (first irradiation range) before limited" (to be referred to as an area ratio hereinafter).

<Index 2>
A dose increase rate R (calculated based on the comparison result by the ABC 7) that is the increase rate of the X-ray dose increased by automatic exposure control at the time of ROI fluoroscopy.

<Index 3>
The product of the "area ratio S2/S1" and the "dose increase rate R".

<Index 4>
A dose rate ratio G2/G1 that is the ratio of an "exposure dose rate (exposure dose rate at the time of ROI fluoroscopy) G2 after limited by the X-ray collimator 1-3" to an "exposure dose rate (exposure dose rate at the time of full field imaging) G1 before limited" (the values G1, G2, and G2/G1 are calculated based on the detected value of the area dose meter 1-2).

<Index 5>
A cumulative value ratio Σ2/Σ1 that is the ratio of a cumulative value (measured value) Σ2 of the exposure dose when ROI fluoroscopy, imaging alternately using ROI fluoroscopy and full field imaging, or ROI fluoroscopy while changing the aperture state of the X-ray collimator 1-3 is actually performed during a predetermined time (the total time of all runs of actual X-ray imaging) to a cumulative value (estimated value) Σ1 of the exposure dose during the predetermined time when full field imaging is assumed to be performed during the predetermined time (the values Σ1, Σ2, and Σ2/Σ1 are calculated based on the detected value of the area dose meter 1-2 and the actual imaging time; the value Σ1 is, for example, an estimated value calculated as the product of the predetermined time and the exposure dose rate by full field imaging, and the value Σ2 is a value measured by the area dose meter 1-2).

A detailed description will be made here by exemplifying a case in which full field imaging is performed from time T1 to time T2, and ROI fluoroscopy is performed from time T2 to time T3.

The cumulative value (estimated value) of the exposure dose when assuming that full field imaging is performed during the time in which ROI fluoroscopy should actually be performed is given by $$\int_{T2}^{T3} G1 \tag{1}$$

The cumulative value of the exposure dose estimated by assuming that only full field imaging is used is given by $$\int_{T1}^{T2} G1 + \int_{T2}^{T3} G1 \tag{2}$$

The cumulative value (measured value) of the exposure dose that is the detected value of the area dose meter 1-2 is given by $$\int_{T1}^{T2} G1 + \int_{T2}^{T3} G2 \quad (3)$$

The reduction rate (cumulative value ratio Σ2/Σ1) of the cumulative value of the exposure dose is calculated as the cumulative value based on the detected value of the area dose meter 1-2/(the cumulative value of the exposure dose when assuming that the ROI fluoroscopy is not used (full field imaging is performed in all runs)) and given by $$\frac{\Sigma 2}{\Sigma 1} = \frac{\int_{T1}^{T2} G1 + \int_{T2}^{T3} G2}{\int_{T1}^{T2} G1 + \int_{T2}^{T3} G1} \quad (4)$$

As is apparent from the above-described expressions, the exposure dose rate G1 at the time of full field imaging that is the past X-ray imaging in chronological terms is used as the reference value when calculating the index representing the X-ray dose reduction effect. The cumulative value Σ1 of the exposure dose, which is calculated as the product of the predetermined time and the dose rate upon the past full field imaging in chronological terms is also used as the reference value when calculating the index representing the X-ray dose reduction effect.

As for updating of the reference value, the reference value is preferably updated each time the operator executes full field imaging. The reference value is also preferably updated each time the observation angle is changed. That is, the higher the frequency of reference value updating is, the higher the reliability of the index representing the X-ray dose reduction is.

Note that the values shown in <1> to <5> are calculated based on the measured value. However, prediction may be done using only the estimated value. An example of such prediction will be described later.

Figure 6:
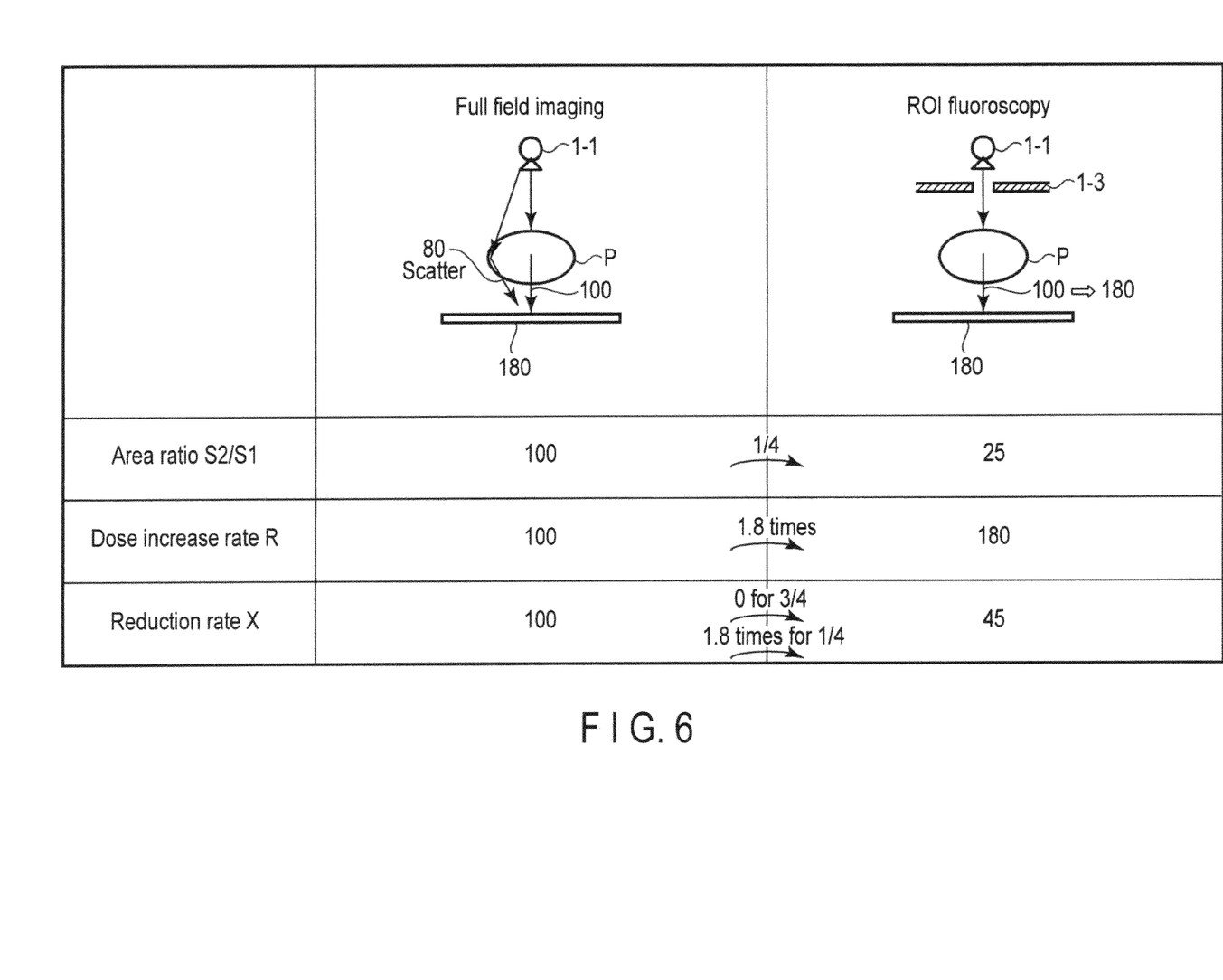
FIG. 6 is a view showing an example of calculation by the reduction rate calculation unit of the X-ray imaging apparatus according to an embodiment of the present invention.

An example of calculation by the dose reduction rate calculation unit 20 will be explained below with reference to FIG. 6. FIG. 6 is a view showing an example of calculation by the reduction rate calculation unit 20 of the X-ray imaging apparatus according to this embodiment. In the example shown in FIG. 6, the values are given by area ratio $S2/S1=25/100=1/4$ dose increase rate $R=180/100=9/5$ reduction rate $X=1/4 \times 9/5=0.45$ However, in the example shown in FIG. 6, the reduction rate X is calculated as the above-described <index 3>, that is, the product of "area ratio S2/S1" and "dose increase rate R".

The reduction rate X=0.45 is represented as 45% as a percentage. This indicates that the exposure dose at the time of ROI fluoroscopy is reduced to 45% of the exposure dose at the time of full field imaging.

The values G1, G2, Σ1, and Σ2 are obtained by the detected value of the area dose meter 1-2 (the output signal of the area dose meter 1-2). As the value of the reduction rate X, a value obtained by calculating G2/G1 or Σ2/Σ1 based on the output signal (detected value) of the area dose meter 1-2 is normally used. As described above, it is possible to obtain the reduction rate X based on various conditions concerning X-ray imaging without using the detected value of the area dose meter 1-2. However, the following advantage can be obtained by using the detected value of the area dose meter 1-2. That is, even when automatic exposure control is executed or the condition of the object has changed in the ROI fluoroscopy, an accurate value can be obtained by using the detected value of the area dose meter 1-2.

The five types of numerical values calculated as in the above-described example are superimposed on the image data or displayed near the image data on the monitor 13. As for the display form of the above-described five types of numerical values, they can be displayed in a form in which, for example, the values are superimposed on the vicinity of the edge of the image data, or a display member other than the monitor 13 is separately provided, and the values are displayed on this display member. Such a display form allows the operator to perform the work while confirming the X-ray dose reduction effect by the X-ray dose reduction processing.

Note that as for the display form of the above-described five types of numerical values, they may be converted into predetermined icons or graphics and displayed, instead of displaying the numerical values themselves. More specifically, the numerical values may be graphically expressed using an "icon used to display the battery level, an "icon used to display the radio wave sensitivity", an "icon imitating a predetermined measuring instrument", and the like used in, for example, a cellular phone and presented to the user.

To more effectively present the X-ray dose reduction effect to the operator, the dose reduction rate calculation unit 20 may create a reduction effect graph representing the X-ray dose reduction effect and display the reduction effect graph superimposed on the image data.

Figure 7:
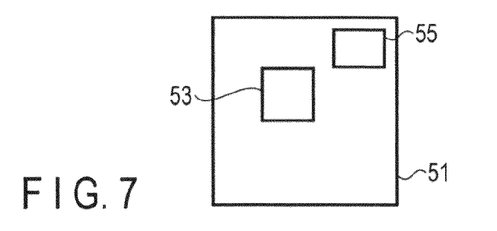
FIG. 7 is a view showing an example of a display area of a reduction effect graph created based on numerical values calculated by the dose reduction rate calculation unit.
Figure 8:
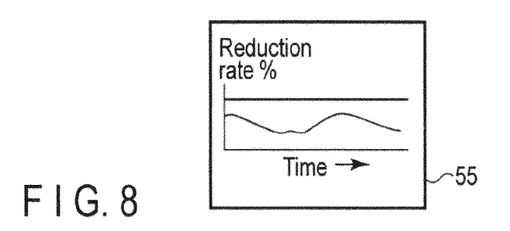
FIG. 8 is a view showing an example of the reduction effect graph displayed in the graph display area.
Figure 9:
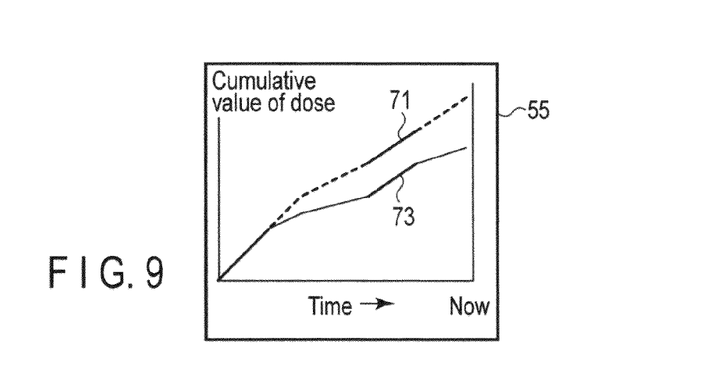
FIG. 9 is a view showing another example of the reduction effect graph displayed in the graph display area.
Figure 10:
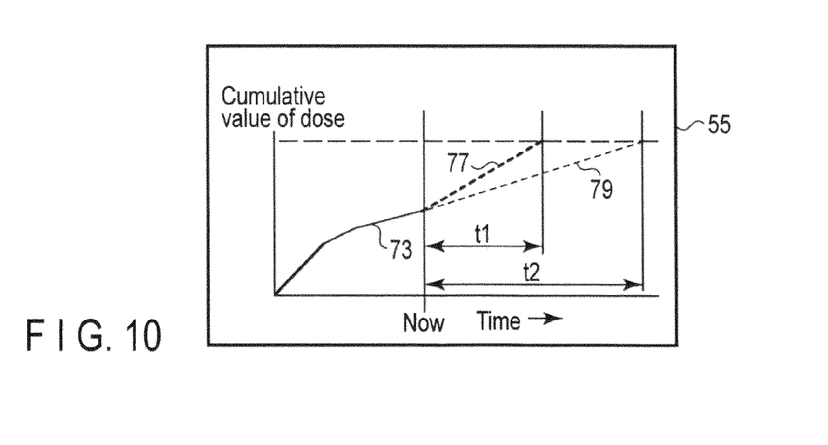
FIG. 10 is a view showing still another example of the reduction effect graph displayed in the graph display area.

The reduction effect graph and its display forms will be described below with reference to FIGS. 7, 8, 9, and 10. FIG. 7 is a view showing an example of an area (to be referred to as a graph display area hereinafter) where the reduction effect graph created based on the above-described numerical values calculated by the dose reduction rate calculation unit 20 is superimposed on the image data and displayed on the monitor 13. FIGS. 8, 9, and 10 are views showing examples of the reduction effect graph displayed in the graph display area. Note that each reduction effect graph is generated by the dose reduction rate calculation unit 20 based on the output value of the area dose meter 1-2, the aperture state of the X-ray collimator 1-3, and the like.

One of the portions most suitable as a graph display area 55 when displaying the reduction effect graph superimposed on the image data on the monitor 13 is a peripheral portion (the upper right portion in the example shown in FIG. 7) of full image data 51, as shown in FIG. 7.

<Real-Time Display>

The first example of the reduction effect graph to be displayed in the graph display area 55 is a "reduction ratio real-time display graph" shown in FIG. 8. In this display example, a graph representing the time-rate change in the value representing the reduction rate X expressed as a percentage is displayed in real time (updated at a predetermined period and displayed). For example, every time the area dose meter 1-2 newly generates and outputs a signal, the display of the reduction rate X is updated to the latest one. The thick solid line in FIG. 8 indicates the exposure dose (predetermined value) at the time of full field imaging, and the thin solid line indicates the ratio (a value expressing the reduction rate X as a percentage) of the exposure dose at the time of ROI fluoroscopy to the exposure dose at the time of full field imaging. In this example, the reduction rate X is obtained as G2/G1.

Note that the update period of the above-described real-time display can be either synchronized with the detection period of the area dose meter 1-2 or different from the detection period.

<Cumulative Value Display (Cumulative Area Dose)>

The second example of the reduction effect graph to be displayed in the graph display area 55 is an "exposure dose cumulative value graph" shown in FIG. 9. In this display example, a graph (second graph 73) representing the time-rate change in the cumulative value obtained by accumulating the value output from the area dose meter 1-2 as the exposure dose of the object P by X-ray imaging (full field imaging and ROI fluoroscopy) during a predetermined period and a graph (first graph 71) representing the cumulative value of the exposure dose when the full field imaging is assumed to be performed during the same time are displayed.

The thick solid line in FIG. 9 indicates the cumulative value of the exposure dose at the time of full field imaging, the thin solid line indicates the cumulative value of the exposure dose at the time of ROI fluoroscopy, and the broken line indicates the cumulative value (the estimated value by the dose reduction rate calculation unit 20) of the exposure dose when assuming that full field imaging is performed in a time zone in which ROI fluoroscopy should actually be performed.

That is, the first graph 71 represents the time-rate change in the cumulative value of the exposure dose when assuming that full field imaging is performed in the entire time zone up to the current point. The second graph 73 represents the time-rate change in the cumulative value of the actual exposure dose by full field imaging and ROI fluoroscopy performed up to the current point.

This display example assumes that the operation is carried out while switching between the full field imaging and the ROI fluoroscopy. At the end of each imaging period (the end of X-ray irradiation), the graph up to the end point of the imaging period is displayed.

<Expected Cumulative Value Display (Predictive Display)>

The third example of the reduction effect graph to be displayed in the graph display area 55 is an "expected cumulative value graph" shown in FIG. 10. In this display example, an expected dose during an assumed time up to the completion of manipulation is displayed. Alternatively, the time until the object P reaches the upper limit of the exposure dose is calculated for each condition (the aperture state of the X-ray collimator 1-3), and a graph representing the time in which X-ray imaging is possible is generated and displayed for each condition.

The thick solid line in FIG. 10 indicates the cumulative value of the exposure dose during the time in which full field imaging is performed, and the thin solid line indicates the cumulative value of the exposure dose at the time of ROI fluoroscopy. The thick broken line indicates the cumulative value (the estimated value by the dose reduction rate calculation unit 20) of the exposure dose when assuming that full field imaging is performed in a time zone in which ROI fluoroscopy should actually be performed. The thin broken line indicates the cumulative value (the estimated value by the dose reduction rate calculation unit 20) of the exposure dose when assuming that ROI fluoroscopy is performed from the current point.

That is, the second graph 73 (thick solid line+thin solid line) represents the time-rate change in the cumulative value of the actual exposure dose by full field imaging and ROI fluoroscopy performed up to the current point. A third graph 77 (thick broken line) represents the time-rate change in the cumulative value of the exposure dose when assuming that full field imaging is performed from the current point. A fourth graph 79 (thin broken line) represents the time-rate change in the cumulative value of the exposure dose when assuming that ROI fluoroscopy is performed from the current point.

The reduction effect graph representing the expected cumulative value is obtained in, for example, the following way. Letting Dmax [Gy·cm$^2$] be the upper limit of the exposure dose of the object P, Dnow [Gy·cm$^2$] be the exposure dose cumulative value of the object P at the current point, D2 [Gy·cm$^2$/sec] be the exposure dose rate by ROI fluoroscopy, and D1 [Gy·cm$^2$/sec] be the exposure dose rate by full field imaging, the graphs are obtained as X-ray imaging enable time $t2$ by ROI fluoroscopy=
($D$max−$D$now)/$D2$ X-ray imaging enable time $t1$ by full field imaging=
($D$max−$D$now)/$D1$ Note that the exposure dose rate D2 [Gy·cm$^2$/sec] by ROI fluoroscopy is a value determined based on the setting of the aperture state of the X-ray collimator 1-3.

Note that for the predictive display graph, a plurality of fourth graphs 79 can be drawn in accordance with the setting of the limited area (collimated amount) of the X-ray irradiation range by the X-ray collimator 1-3. Hence, a plurality of collimated amounts may be set by the X-ray collimator 1-3 (for example, the collimated amount at the current point, the collimated amount when the X-ray irradiation range is limited to ¼ that at the time of full field imaging, and the like), and a plurality of fourth graphs 79 corresponding to the settings may be drawn.

When the graph that predicts the time-rate change in the cumulative value from the current point is created and displayed in the above-described manner, the operator can easily recognize the X-ray imaging enable time under each condition.

As described above, according to this embodiment, there are provided an X-ray imaging apparatus that allows the operator to recognize the degree of exposure dose reduction implemented by executing ROI fluoroscopy as compared to a case in which normal X-ray imaging apparatus is (to be) executed, and a program.

Note that this embodiment may be implemented as a form in which, for example, when calculating various values such as the reduction rate X, simulation is calculated in advance using a desired estimated value instead of using the output value (measured value) of the area dose meter 1-2 as the dose.

As the X-ray dose reduction method, any other X-ray dose reduction method may be used simultaneously in addition to the above-described X-ray irradiation range limiting (ROI fluoroscopy) using the X-ray collimator 1-3, as a matter of course. For example, an X-ray dose reduction method by changing various conditions such as the tube current, the tube voltage, the pulse width, the SID (the distance between the X-ray source and the detector), the PID (Patient Imager Distance) (the distance between the patient and the detector), the beam quality filter, the collimator, and the FOV (Field Of View) may be used simultaneously in addition to the above-described ROI fluoroscopy.

When the series of processes by the X-ray imaging apparatus according to the above-described embodiment is programmed, or a program obtained by the programming is stored in a storage medium, a stand-alone software product independent of the X-ray imaging apparatus can easily be sold or distributed. This also enables to use the technique according to this embodiment on another hardware.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray imaging apparatus for performing X-ray imaging of an object and acquiring an X-ray fluoroscopic image, comprising:
    an X-ray generation unit configured to irradiate the object with X-rays;
    an X-ray collimator configured to limit an X-ray irradiation range of the X-ray generation unit;
    a dose detection unit configured to detect the X-rays that have passed through the X-ray collimator;
    a dose reduction rate calculation unit configured to calculate a reduction rate of an exposure dose of the object based on a value detected by the dose detection unit in X-ray imaging before the X-ray irradiation range is limited by the X-ray collimator and a value detected by the dose detection unit in X-ray imaging after the X-ray irradiation range is limited by the X-ray collimator;
    a display unit configured to display a graph based on the reduction rate,
    wherein the display unit displays at least one of a full field imaging expected cumulative value graph and a limited field imaging expected cumulative value graph as the graph, the full field imaging expected cumulative value graph representing time-rate change in a cumulative value of the exposure dose when assuming that X-ray imaging is performed without limitation of the X-ray irradiation range by the X-ray collimator from a current point, and the limited field imaging expected cumulative value graph representing time-rate change in a cumulative value of the exposure dose when assuming that X-ray imaging is performed with limitation of the X-ray irradiation range by the X-ray collimator from the current point.

2. The apparatus according to claim 1, wherein the dose reduction rate calculation unit calculates, as the reduction rate, a value G2/G1 when an exposure dose rate detected by the dose detection unit in the X-ray imaging before the X-ray irradiation range is limited by the X-ray collimator is defined as a reference value G1, and an exposure dose rate detected by the dose detection unit in the X-ray imaging after the X-ray irradiation range is limited by the X-ray collimator is defined as a current value G2.

3. The apparatus according to claim 2, wherein the dose reduction rate calculation unit calculates, as the reduction rate, a value $\Sigma2/\Sigma1$ when a cumulative value of the exposure dose detected by the dose detection unit in X-ray imaging for a predetermined time is defined as a measured cumulative value $\Sigma2$, and a product of the predetermined time and a dose rate detected by the dose detection unit in X-ray imaging performed without causing the X-ray collimator to limit the X-ray irradiation range before execution of the X-ray imaging for the predetermined time is defined as a reference cumulative value $\Sigma1$.

4. The apparatus according to claim 1, further comprising a display unit configured to display the reduction rate together with the X-ray fluoroscopic image.

5. The apparatus according to claim 1, further comprising:
    a storage unit configured to store an upper limit of the cumulative value of the exposure dose permitted for the object; and
    an imaging enable time calculation unit configured to calculate a time needed until the cumulative value of the exposure dose of the object changes from a value at the current time to the upper limit when assuming that the X-ray imaging at the exposure dose rate corresponding to the X-ray irradiation range limited to the predetermined area by the X-ray collimator is performed from the current time,
    wherein the display unit displays a graph representing the upper limit and the time needed to reach the upper limit.

6. The X-ray imaging apparatus according to claim 1, wherein the display unit displays both of the full field imaging expected cumulative value graph and the limited field imaging expected cumulative value graph on a single screen.

7. The X-ray imaging apparatus according to claim 1, wherein the display unit displays an actual cumulative value graph representing time-rate change in a cumulative value of the exposure dose of the object up to the current point in addition to the at least one of the full field imaging expected cumulative value graph and the limited field imaging expected cumulative value graph on a single screen.

* * * * *